US011862340B2

United States Patent
Sinha et al.

(10) Patent No.: US 11,862,340 B2
(45) Date of Patent: Jan. 2, 2024

(54) METHOD AND SYSTEM FOR CARDIOVASCULAR DISEASE ASSESSMENT AND MANAGEMENT

(71) Applicant: Riva Health, Inc., Burlingame, CA (US)

(72) Inventors: Tuhin Sinha, Burlingame, CA (US); Ian Eslick, Burlingame, CA (US); Alan Leggitt, Burlingame, CA (US)

(73) Assignee: Riva Health, Inc., Burlingame, CA (US)

( * ) Notice: Subject to any disclaimer, the term of this patent is extended or adjusted under 35 U.S.C. 154(b) by 0 days.

(21) Appl. No.: 17/866,185

(22) Filed: Jul. 15, 2022

(65) Prior Publication Data

US 2022/0375613 A1 Nov. 24, 2022

Related U.S. Application Data

(60) Continuation of application No. 16/538,206, filed on Aug. 12, 2019, now Pat. No. 11,424,032, which is a (Continued)

(51) Int. Cl.
*A61B 5/02* (2006.01)
*G16H 50/20* (2018.01)
(Continued)

(52) U.S. Cl.
CPC ......... *G16H 50/20* (2018.01); *A61B 5/02108* (2013.01); *A61B 5/02116* (2013.01);
(Continued)

(58) Field of Classification Search
CPC .............. A61B 5/0077; A61B 5/02108; A61B 5/02427; A61B 5/02438; A61B 5/4812;
(Continued)

(56) References Cited

U.S. PATENT DOCUMENTS

| 5,649,543 A | 7/1997 | Hosaka et al. |
| 6,337,629 B1 | 1/2002 | Bader |

(Continued)

FOREIGN PATENT DOCUMENTS

| CN | 103826532 A | 5/2014 |
| CN | 104337509 A | 2/2015 |

(Continued)

OTHER PUBLICATIONS

"Clinical Validation of Tele-stethoscope System Digital", https://clinicaltrials.gov/ct2/show/study/NCT03596541, first posted Jul. 24, 2018.

(Continued)

*Primary Examiner* — Amanda K Hulbert
(74) *Attorney, Agent, or Firm* — Jeffrey Schox; Randy Mehlenbacher

(57) ABSTRACT

An embodiment of a method for assessing cardiovascular disease in a user with a body region using a mobile computing device including a camera module, includes receiving a time series of image data of a body region of the user, the time series of image data captured during a time period; generating a photoplethysmogram dataset from the time series of image data; generating a processed PPG dataset; determining a cardiovascular parameter value of the user based on the processed PPG dataset; fitting a chronobiological model to (1) the cardiovascular parameter value, and (2) a subsequent cardiovascular parameter value, characterizing a cardiovascular parameter variation over time of the user based on the fitted chronobiological model; and presenting an analysis of the cardiovascular parameter variation to the user at the mobile computing device.

13 Claims, 7 Drawing Sheets

Related U.S. Application Data division of application No. 15/183,285, filed on Jun. 15, 2016, now Pat. No. 10,420,475.

(60) Provisional application No. 62/175,971, filed on Jun. 15, 2015.

(51) Int. Cl.
| | |
|---|---|
| A61B 5/021 | (2006.01) |
| A61B 5/00 | (2006.01) |
| A61B 5/024 | (2006.01) |
| G16H 50/30 | (2018.01) |
| G16H 30/40 | (2018.01) |
| G16H 50/50 | (2018.01) |
| G16H 40/67 | (2018.01) |
| G16H 30/20 | (2018.01) |
| G06N 7/01 | (2023.01) |
| G06N 20/00 | (2019.01) |

(52) U.S. Cl.
CPC ........ *A61B 5/02427* (2013.01); *A61B 5/4812* (2013.01); *A61B 5/4857* (2013.01); *A61B 5/6898* (2013.01); *A61B 5/7264* (2013.01); *G06N 7/01* (2023.01); *G16H 30/20* (2018.01); *G16H 30/40* (2018.01); *G16H 40/67* (2018.01); *G16H 50/30* (2018.01); *G16H 50/50* (2018.01); *A61B 5/0077* (2013.01); *A61B 5/02405* (2013.01); *A61B 5/02416* (2013.01); *A61B 5/02438* (2013.01); *G06N 20/00* (2019.01)

(58) Field of Classification Search
CPC .............. A61B 5/7264; A61B 2576/00; A61B 5/02055; A61B 5/02116; A61B 5/02405; A61B 5/02416; A61B 5/4857; A61B 5/6826; A61B 5/6843; A61B 5/6898; A61B 5/7221; A61B 5/7239; A61B 5/7275; G06F 19/30; G06N 20/00; G06N 7/005; G01R 17/105; G01R 19/25; G01R 27/02; G16H 20/10; G16H 20/70; G16H 30/40; G16H 40/63; G16H 50/20; G16H 50/30; H03M 1/46; H03M 1/742; H03M 3/00; H03M 3/04; H03M 3/458
See application file for complete search history.

(56) References Cited

U.S. PATENT DOCUMENTS

| | | | |
|---|---|---|---|
| 6,475,153 | B1 | 11/2002 | Khair et al. |
| 6,993,377 | B2 | 1/2006 | Flick et al. |
| 7,286,875 | B1 | 10/2007 | Park et al. |
| 7,787,946 | B2 | 8/2010 | Stahmann et al. |
| 8,239,010 | B2 | 8/2012 | Banet et al. |
| 8,761,853 | B2 | 6/2014 | Thaveeprungsriporn et al. |
| 10,420,515 | B2 | 9/2019 | Sinha et al. |
| 2003/0163057 | A1 | 8/2003 | Flick et al. |
| 2008/0045818 | A1 | 2/2008 | Wood et al. |
| 2009/0326386 | A1 | 12/2009 | Sethi et al. |
| 2010/0168589 | A1 | 7/2010 | Banet et al. |
| 2011/0066051 | A1 | 3/2011 | Moon et al. |
| 2011/0077531 | A1 | 3/2011 | Addison et al. |
| 2011/0224564 | A1 | 9/2011 | Moon et al. |
| 2012/0029320 | A1 | 2/2012 | Watson et al. |
| 2012/0179011 | A1 | 7/2012 | Moon et al. |
| 2012/0190947 | A1 | 7/2012 | Chon et al. |
| 2013/0276785 | A1 | 10/2013 | Melker et al. |
| 2013/0310656 | A1 | 11/2013 | Lim et al. |
| 2013/0345568 | A1 | 12/2013 | Mestha et al. |
| 2014/0003454 | A1 | 1/2014 | Kaemmerer et al. |
| 2014/0275854 | A1 | 9/2014 | Venkatraman et al. |
| 2014/0278220 | A1 | 9/2014 | Yuen |
| 2014/0303454 | A1 | 10/2014 | Clifton et al. |
| 2015/0037937 | A1 | 2/2015 | Park et al. |
| 2015/0080746 | A1 | 3/2015 | Bleich et al. |
| 2015/0182132 | A1 | 7/2015 | Harris et al. |
| 2015/0324977 | A1 | 11/2015 | Magrath et al. |
| 2015/0379370 | A1 | 12/2015 | Clifton et al. |
| 2016/0058375 | A1 | 3/2016 | Rothkopf |
| 2016/0256117 | A1 | 9/2016 | Baik et al. |
| 2016/0302674 | A1 | 10/2016 | Moyer et al. |
| 2016/0360980 | A1 | 12/2016 | Sinha et al. |
| 2017/0007137 | A1 | 1/2017 | Hong et al. |
| 2017/0071516 | A1 | 3/2017 | Bhagat et al. |
| 2017/0079533 | A1 | 3/2017 | Robinson et al. |
| 2018/0146865 | A1 | 5/2018 | Ortlepp |
| 2019/0059753 | A1 | 2/2019 | Chen et al. |
| 2019/0175120 | A1 | 6/2019 | Huang |

FOREIGN PATENT DOCUMENTS

| | | |
|---|---|---|
| EP | 2992820 A2 | 3/2016 |
| KR | 20160028093 A | 3/2016 |
| WO | 2014022906 A1 | 2/2014 |
| WO | 2015193551 A1 | 12/2015 |

OTHER PUBLICATIONS

"National Institute of Health and Nutrition Examination Survey (NHANES)", Health Tech/Blood Pressure Procedures Manual, May 2009.

"Non-invasive sphygmomanometers—Part 2: Clinical investigation of intermittent automated measurement type", International Standard, ISO 81060-2, Third edition Nov. 2018.

Elgendi, Mohamed, "Merging digital medicine and economics: Two moving averages unlock biosignals for better health", Diseases 6.1 (2018): 6. (Year: 2018).

Lai, Lillian S.W., et al., "Computerized Automatic Diagnosis of Innocent and Pathologic Murmurs in Pediatrics: A Pilot Study", Congenital Heart Dis. 2016; 11:386-395.

Lee, Han-Wook, et al., "he periodic moving average filter for removing motion artifacts from PPG signals", International Journal ofControl, Automation, and Systems 5.6 (2007): 701-706. (Year: 2007).

Perpetuini, David, et al., "Multi-site photoplethysmographic and electrocardiogram for arterial stiffness and cardiovascular status assessment", Sensors 19.24 (2019): 5570. (Year: 2019).

Rojano, Juan F., "Singular value decomposition of the time-frequency distribution of PPG signals for motion artifact reduction", Int. J. Signal Process. Syst 4.6 (2016): 475-482. (Year: 2016).

Scholze, A., et al., "Increased arterial vascular tone during the night in patients with essential hypertension", Journal of Human Hypertension (2007) 21, 60-67. published online 5 October. [retrieved on Aug. 22, 2016] retrieved from the Internet : http://www.nature.com.

Stergiou, George S., et al., "A Universal Standard for the Validation of Blood Pressure Measuring Devices", Hypertension, Mar. 2018;71(3):368-374, doi: 10.1161/HYPERTENSIONAHA.117. 10237. Epub Jan. 31, 2018.

Stergiou, George S., et al., "Validation protocols for blood pressure measuring devices in the 21st century", J Clin Hypertens. 2018;20:1096-1099.

Sugita, Norihiro, et al., "Techniques for estimating blood pressure variation using video images", 37th Annual International Conference of the IEEE Engineering in Medicine and Biology Society (EMBC) Aug. 29, 2015.

Trafton, Anne, "In the blink of an eye, MIT neuroscientists find the brain can identify images seen for an as little as 13 milliseconds", MIT News, Jan. 16, 2014.

Vadrevu, Simhadri, et al., "A robust pulse onset and peak detection method for automated PPG signal analysis system", IEEE Transactions on Instrumentation and Measurement 68.3 (2018): 807-817. (Year: 2018).

Wang, Lu, et al., "Multi-Gaussian fitting for pulse waveform using weighted least squares and multi-criteria decision making method", Computers in biology and medicine 43.11 (2013): 1661-1672. (Year: 2013).

Wu, Hongiun, et al., "A New Automatic blood pressure kit auscultates for accurate reading with a smartphone", Medicine (2016) 95:32.

S250

8 harmonic cosigner model fitted to each beat

S260

METHOD AND SYSTEM FOR CARDIOVASCULAR DISEASE ASSESSMENT AND MANAGEMENT

CROSS-REFERENCE TO RELATED APPLICATIONS

This application is a continuation of U.S. application Ser. No. 16/538,206, filed 12 Aug. 2019, which is a divisional application of U.S. Application Ser. No. 15/183,285, filed 15 Jun. 2016, which claims the benefit of U.S. Provisional Application Ser. No. 62/175,971 filed 15 Jun. 2015, each of which is incorporated in its entirety herein by this reference.

TECHNICAL FIELD

This invention relates generally to the field of cardiovascular disease, and more specifically to a new and useful method and system for analyzing data captured over time for assessment and management of cardiovascular disease.

BACKGROUND

The total market size for cardiovascular disease (CVD) is approximately $600 billion, with one in three American adults suffering from one or more types of CVD. It has been estimated that the total costs of hypertension (HTN) alone exceed $90 billion, including costs for medications, unnecessary complications, emergency department visits, and hospitalization. In most cases, patients with HTN are co-morbid with other conditions, and HTN can indicate risk of aneurysms, heart attack, stroke kidney failure, metabolic syndrome, heart failure, and other types of CVD; thus, CVD is a tremendous burden to the healthcare system.

Unfortunately, current standards of CVD assessment and management are fraught with inefficiencies, and technologies for assessing, managing, and treating CVD are substantially outdated. In particular, patient access between office visits/hospitalizations is limited or non-existent, which is exacerbated by the declining supply of general cardiologists and the growing demand of cardiology patients. Additional factors contribute to deficiencies in current methods of providing remote management of patients with CVD-related conditions. There is thus a need in the field of cardiovascular disease to create a new and useful method and system for assessment and management of cardiovascular disease. This invention provides such a new and useful method and system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 2:
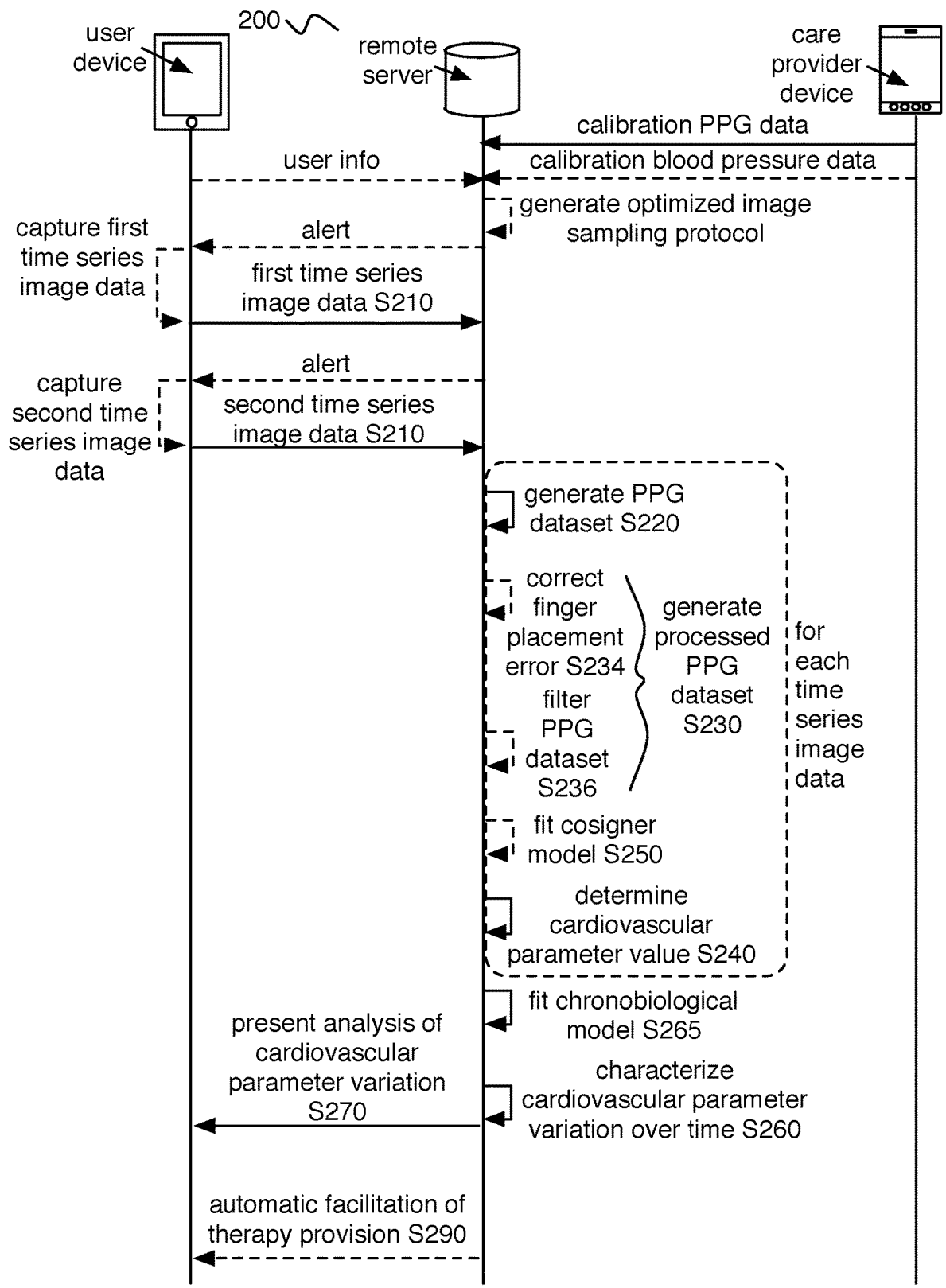
FIG. 2 depicts an application flow of an embodiment of a method for monitoring and assessing cardiovascular disease.
Figure 3:
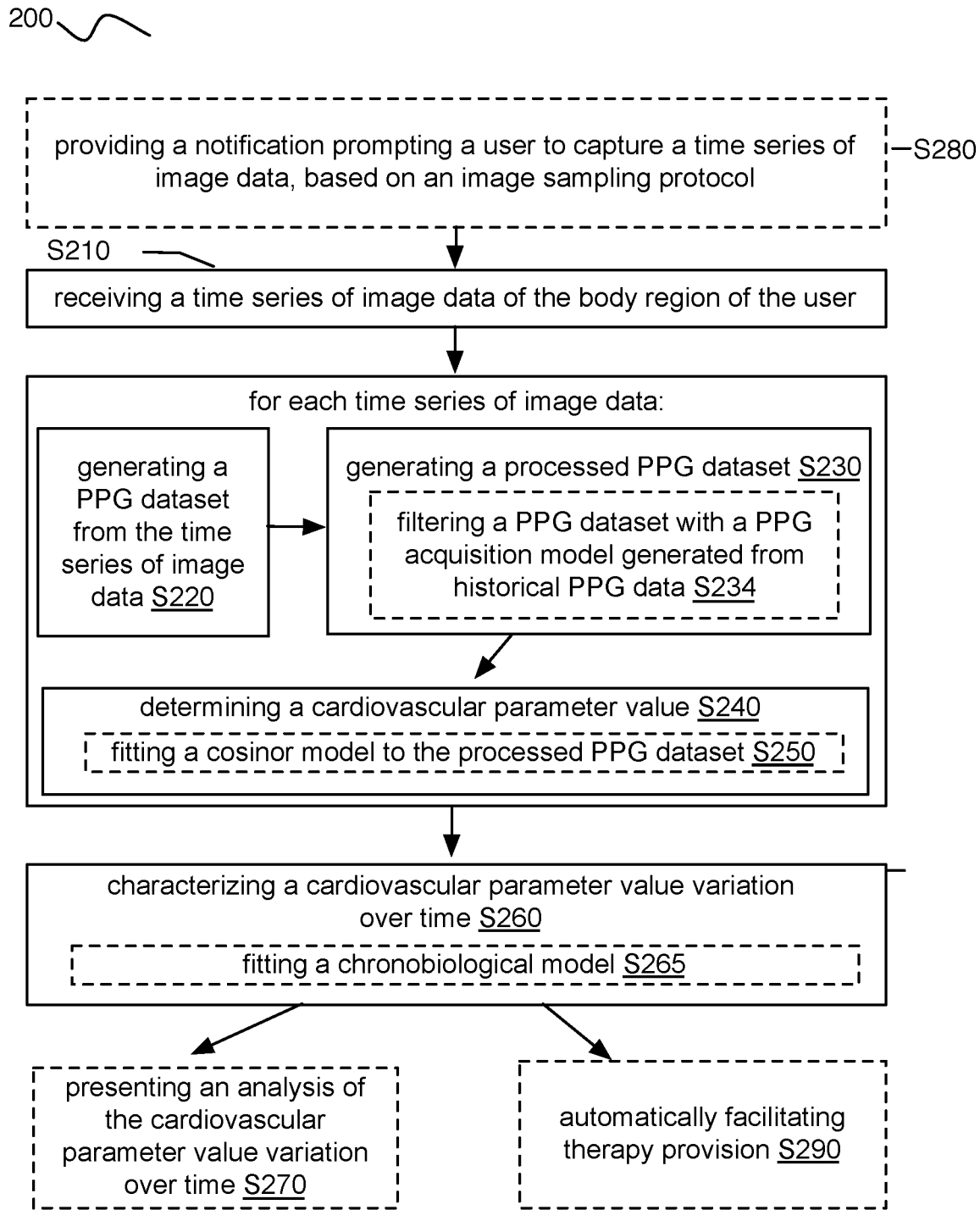
FIG. 3 depicts an application flow of an embodiment of a method for monitoring and assessing cardiovascular disease.
Figure 8:
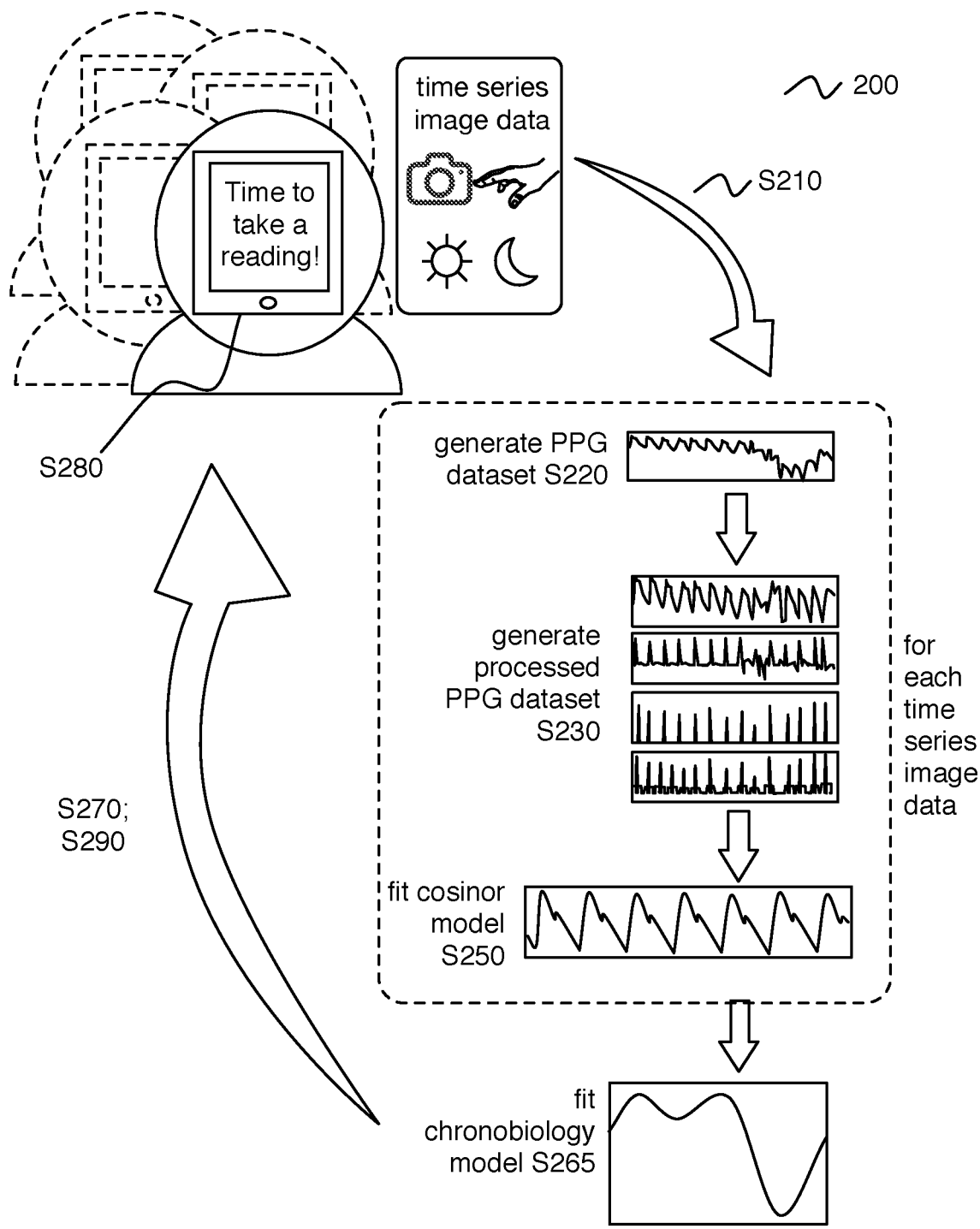
FIG. 8 depicts an application flow of an embodiment of a method for monitoring and assessing cardiovascular disease.

As shown in FIGS. 2-3 and 8, an embodiment of a method 200 for assessing cardiovascular disease in a user using a camera module, the method including: receiving a time series of image data S210 of a body region of the user, the time series of image data captured during a time period; generating a photoplethysmogram (PPG) dataset from the time series of image data S220; generating a processed PPG dataset S230; determining a cardiovascular parameter value of the user based on the processed PPG dataset S240; fitting a chronobiological model S265 to (1) the cardiovascular parameter value, and (2) a subsequent cardiovascular parameter value, characterizing a cardiovascular parameter variation over time of the user based on the fitted chronobiological model S260; and presenting an analysis of the cardiovascular parameter variation to the user at a mobile computing device associated with the camera module S270. While variations of the method 100 implement a mobile computing device comprising a camera module, some variations of the method 100 can alternatively omit use of a mobile computing device camera module.

In some variations, the method 200 functions to assess cardiovascular disease-related health states in a user using a mobile computing device with a camera module. The method 200 can further function to alert a user, a care provider, and/or any other suitable entity of cardiovascular risks identified in a user. The method 200 can additionally or alternatively function to automatically facilitate therapy provision to a user based on analysis of determined cardiovascular parameter variation. The method 200 is preferably performed with an embodiment, variation, or example of the system 100 described below, but can alternatively be performed with any other suitable system 100.

2. Benefits.

In specific examples, the system 100 and/or method 200 can confer several benefits over conventional methodologies for determining and cardiovascular parameters for managing cardiovascular disease. In specific examples, the system 100 and/or method 200 can perform one or more of the following:

First, the technology can provide a convenient, frictionless user experience. For example, rather than requiring an external device usually coupled to a smart phone, portions of the method 200 can be implemented with consumer smartphone devices (or other mobile computing devices). In specific examples, cardiovascular parameters and cardiovascular risks can be determined based on image data captured from a smartphone camera by a user. Such implementation can reduce the need for user-specific a priori calibration using statistical modeling of population data across demographics and disease. In variations, the method 200 can be performed without supplementary electrocardiogram datasets, circumventing the need for an ECG biosignal detector.

Second, the technology can improve upon existing sensor technology by improving specificity in ascertaining and managing cardiovascular disease burden in individuals. Such specificity can aid in providing targeted therapies to patients. For example, improvements in specificity can be ascertained in determining cardiovascular parameters such as: heart rate, heart rate variability, blood pressure, blood pressure variability, measures of blood vessel stiffness, measures indicative of atherosclerosis, and/or other relevant cardiovascular parameters indicative of cardiovascular risk.

Third, the technology can leverage imaged-derived signal processing technologies to specifically determine and assess cardiovascular parameters in order to enable automatic facilitation of therapy provision, including: modulating medication provision, automatically adjusting environmental aspects of the user to promote health of the user, providing tailored medical recommendations, facilitating digital communications between patients and care providers, and/or any suitable therapy provision for managing cardiovascular disease.

Fourth, the technology can confer improvements to the technological areas of at least biosensors, leveraging mobile computing device technology to determine cardiovascular parameters, and digital management of cardiovascular disease. Such improvements can be conferred through, for example, the facilitation of self- and/or remote-cardiovascular health monitoring, enabling a more convenient user experience for improving user adherence. Further, a frictionless user experience can be provided while maintaining a sufficient level of specificity of physiological monitoring of cardiovascular disease-related health states, in order to enable automatic, tailored therapy provision.

Fifth, the technology can confer improvements in a mobile computing device itself that is implementing one or more portions of the method 200, as the mobile computing device can be transformed into a biosignal detector with high specificity in determining relevant cardiovascular parameters and/or managing cardiovascular disease. In examples, the technology can enable cardiovascular parameter evaluation using fewer sources of data (e.g., without electrocardiogram data), thus requiring computing systems to process fewer types of data.

Sixth, the technology can provide technical solutions necessarily rooted in computer technology (e.g., leveraging a mobile computing device to capture image data; transforming image data to different states such as raw and processed biosignals used for determining cardiovascular status of individuals; automatically facilitating therapy provision based on such data, etc.) to overcome issues specifically arising with computer technology (e.g., how to leverage mobile computing systems for cardiovascular management in a user-frictionless manner; how to allow computer systems to determine certain cardiovascular parameters using fewer types of data; how to facilitate digital communication of time-sensitive data amongst a system of computing systems, in order to enable automatic therapy provision in situations where the patient is at risk, etc.).

The technology can, however, provide any other suitable benefit(s) in the context of using non-generalized computer systems for digital health applications.

3. System.

Figure 1:
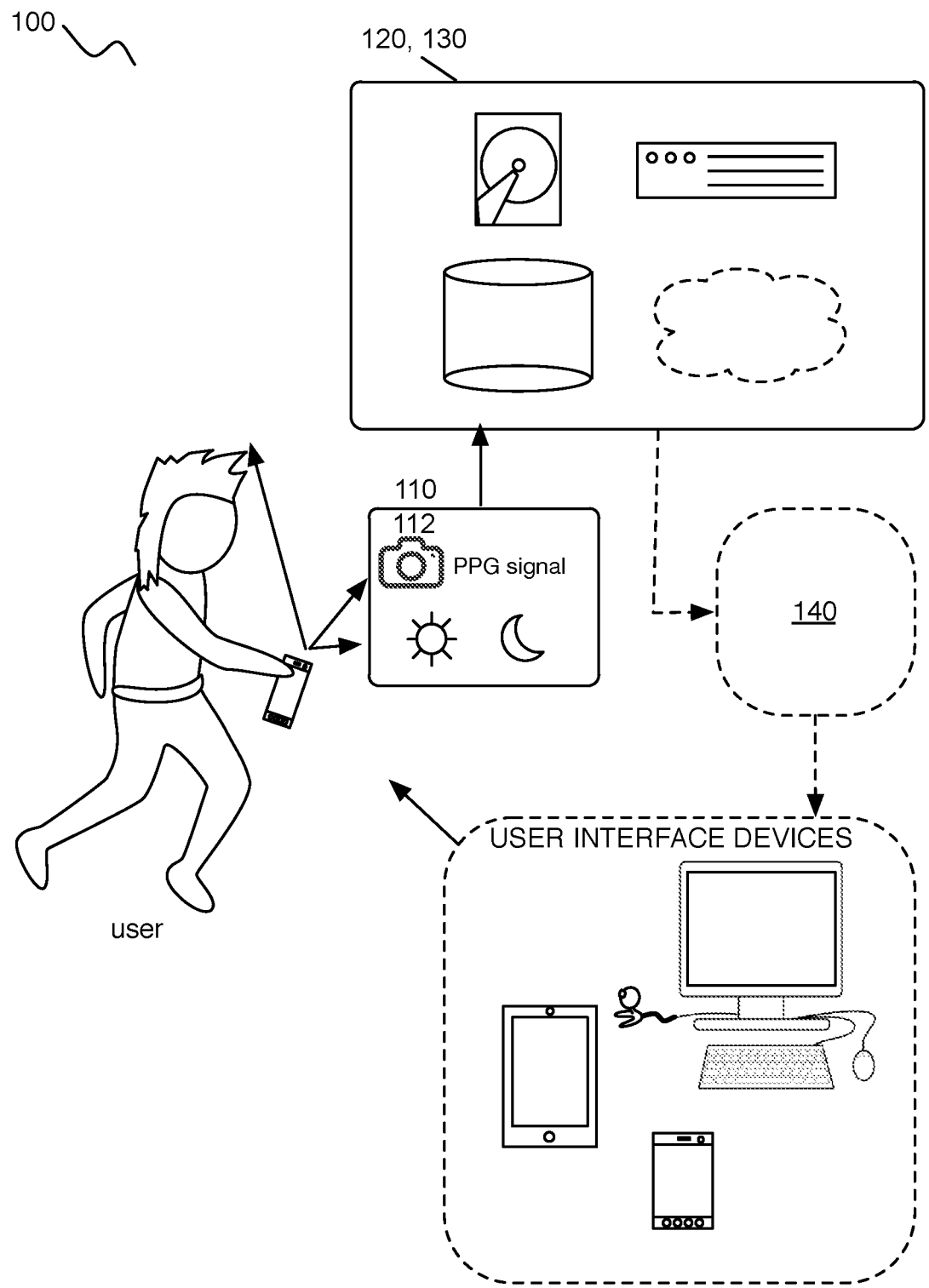
FIG. 1 depicts an embodiment of a system for monitoring and assess cardiovascular disease.

As shown in FIG. 1, an embodiment of a system 100 for assessing cardiovascular risks in a user can include a data collection module 110, a data processing module 120, a data analysis module 130, and an output module 140.

The system 100 functions to determine cardiovascular parameter variations (e.g., diurnal blood pressure variations, variations in other cardiovascular parameters, etc.) of a user over time through analysis of data collected at a mobile computing system with a camera module 112. The system 100 preferably enables or otherwise performs an embodiment, variation, or example of the method 200 described above, but can alternatively facilitate performance of any suitable method involving determination of cardiovascular parameter variation over time.

In some embodiments, the system 100 can additionally or alternatively include or communicate data to and/or from: a user database (storing user account information, user profiles, user health records, user demographic information, associated care provider information, associated guardian information, user device information, etc.), an analysis database (storing computational models, collected data, historical signal data, public data, simulated data, determined cardiovascular parameters, etc.), and/or any other suitable computing system.

Database(s) and/or portions of the method 200 can be entirely or partially executed, run, hosted, or otherwise performed by: a remote computing system (e.g., a server, at least one networked computing system, stateless computing system, stateful computing system, etc.), a user device (e.g., a device of a user executing an application for collecting data and determining associated cardiovascular parameters), a care provider device (e.g., a device of a care provider associated with a user of the application executing on the user device), a machine configured to receive a computer-readable medium storing computer-readable instructions, or by any other suitable computing system possessing any suitable component (e.g., a graphics processing unit, a communications module, etc.). However, the modules of the system 100 can be distributed across machine and cloud-based computing systems in any other suitable manner.

Devices implementing at least a portion of the method 200 can include one or more of: a smartwatch, smartphone, a wearable computing device (e.g., head-mounted wearable computing device), tablet, desktop, a camera module 112, a supplemental sensor, a biosignal detector, an implantable medical device, an external medical device, and/or any other suitable device, as described in more detail below. All or portions of the method 200 can be performed by one or more of: a native application, web application, firmware on the device, plug-in, and any other suitable software executing on the device. Device components used with the method 200 can include an input (e.g., keyboard, touchscreen, etc.), an output (e.g., a display), a processor, a transceiver, and/or any other suitable component, wherein data from the input device(s) and/or output device(s) can be collected and/or transmitted to entities for analysis (e.g., to determine cardiovascular parameter variation over time). Communication between devices and/or databases can include wireless communication (e.g., WiFi, Bluetooth, radiofrequency, etc.) and/or wired communication.

The data collection module 110, data processing module 120, data analysis module 130, output module 140, any other suitable component of the system 100, and/or any suitable step of the method 200 can employ machine learning approaches including any one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each processing portion of the method 200 can additionally or alternatively leverage: a probabilistic module, heuristic module, deterministic module, or any other suitable module leveraging any other suitable computation method, machine learning method or combination thereof.

3.1 Data Collection Module

As shown in FIG. 1, the data collection module 110 functions to collect data for processing and analysis in order to determine cardiovascular parameters of the user. The data collection module 110 preferably includes a camera module 112 and a signal generation module. Additionally or alternatively, the data collection module no can include: a biosignal detector (e.g., a heart rate monitor, etc.), a supplemental sensor (e.g., a sensor of a smartphone, a sensor of a wearable fitness device, etc.), and/or any other suitable component.

3.1.A Camera Module

With respect to variations where the data collection module 110 includes a camera module 112, the camera module 112 preferably includes at least one camera unit 112 configured to generate image data and/or video data from a body region (e.g., a finger region a head region, and/or any suitable human body region) of the individual. The camera module 112 is preferably a component of a mobile computing system associated with a user, but can additionally or alternatively be a component of a mobile computing system associated with a care provider, an organization, a guardian, and/or any other suitable entity. The camera module 112 can alternatively be a component distinct from a mobile computing system, but can otherwise take any suitable form. Additionally or alternatively, the camera module 112 can include a second camera unit configured to generate ambient light data for normalization of the time series of image data. However, the camera module 112 and associated image data can possess any suitable characteristic.

Image data captured from the camera module 112 and/or supplementary sources can include: a single image, a composite image (e.g., mosaic including multiple images stitched together), a time series of image data (e.g., multiple images captured in series over time), a video, multi-dimensional image data, graphics, patterns, animations, and/or any other suitable static or moving image data. The image data can be of any suitable type (e.g., vector images, raster images, multispectral images, ultraspectral images, etc.), have any suitable color characteristic (e.g., color, black and white, multiple color channels, image intensity, etc.), resolution characteristic, multi-dimensional characteristic, and/or any suitable image parameter.

The image data is preferably associated with one or more temporal indicators (e.g., a time point, a time period, a time unit, etc. The temporal indicator can be a time point relative to a time period, an absolute time (e.g., indicated by a global timestamp), or any other suitable measure of time. The time period is preferably associated with a feature of a human day (e.g., a daytime period, a nighttime period, a sleeping phase, a waking phase, a morning, an afternoon, a night, a sunrise, a sunset, a dawn, a dusk, a twilight, etc.), but can additionally or alternatively be associated with any other suitable feature. In a first example, a daytime period includes the time from sunrise to sunset, and the nighttime period includes the time from sunset to sunrise. In a second example, a sleeping phase can include: stage 1, 2, 3, 4, and/or rapid eye movement sleep. The time period can include any suitable duration of time (e.g., a second, minute, hour, day, week, month, year, etc.), which can be a continuous duration (e.g., a continuous 24 hour period), or a non-continuous duration (e.g., a 24 hour period composed of different hours of different days). The temporal indicator can additionally or alternatively describe time in relation to any suitable reference point (e.g., number of hours after awakening, after sleeping, after sunrise, after sunset, etc.). However, temporal indicators can possess any suitable characteristic, and can be associated with any suitable data structure (e.g., PPG data, cardiovascular parameters, analyses of cardiovascular parameters, notifications, therapy provision, etc.) and/or component.

The image data is preferably received at a remote computing system that stores and processes the image data. Alternatively, the image can be entirely or partially processed at a user mobile computing device, but can additionally or alternatively be received and/or processed at any suitable component. The image data preferably includes a set of image elements. Types of image elements can include a pixel, a superpixel, a digital value, an image segment, or any other suitable image element. Alternatively, the image includes a single image element. However, the image can include any number of image elements defined in any suitable fashion.

3.1.B Signal Generation Module

With respect to variations where the data module no includes a signal generation module, the signal generation module preferably converts image data captured by the camera module 112 into a raw signal indicating a biological characteristic of a user. The raw signal preferably includes a PPG signal, but can additionally or alternatively include any other signal. When the raw signal includes a PPG signal, the PPG signal preferably arises from optical measurement of illuminated tissue (e.g., tissue structures perfused with blood). Additionally or alternatively, the signal module can convert image data that does not originate from the camera module 112, such as public image data of body regions of patients. However, the signal generation module can leverage any suitable image data to generate any suitable type of signal.

3.2 Data Processing Module

As shown in FIG. 1, the data processing module 120 functions to process image data and/or raw signals (e.g., a PPG dataset) in order to generate a processed dataset for analysis by the data analysis module 130 in determining a cardiovascular parameter of the user. The data processing module 120 is preferably implemented at a remote server, but can additionally or alternatively be implemented at a mobile computing device of the user and/or any other computing system. The data processing module 120 preferably performs processing on a PPG dataset generated by the signal generation module from image data captured by the camera module 112, but the data processing module 120 can additionally or alternatively process any other suitable dataset (e.g., non-PPG datasets, ECG datasets, PPG datasets collected from other sources, etc.). The data processing module 120 can perform operations associated with embodiments, variations, or examples of the method 200 described including one or more of: normalization, filtering, noise reduction, smoothing, model fitting, transformations, mathematical operations (e.g., calculating a first derivative of collected signals, positive component squared operations, operations associated with moving averages, etc.), image processing, and/or any other suitable processing. During operation, the data processing module 120 can additionally or alternatively correct for one or more of: body region placement errors with respect to captured image data by the camera module 112 (e.g., a misplaced finger relative a camera module 112 of a user smartphone camera), variations in motion of the mobile computing device or other components of the system 100 (e.g., a user who shakes the mobile computing device during video capture of a finger for cardiovascular analysis), fingertip pressure, and/or any other suitable issues related to data collection. However, the data processing module 120 can generate a processed dataset in any other suitable manner.

3.3 Data Analysis Module

As shown in FIG. 1, the data analysis module 130 functions to analyze one or more datasets in determining a cardiovascular parameter value of a user. The data analysis module 130 is preferably implemented at the remote server implementing the data processing module 120, but can additionally or alternatively be implemented at any suitable computing system. The data analysis module 130 is preferably configured to analyze processed datasets (e.g., a processed PPG dataset) generated from the data processing module 120. Additionally or alternatively, the data analysis module 120 can analyze processed datasets with supplemental datasets (e.g. user demographic data inputted by the user, supplemental biosignal datasets, motion data, physical activity data, etc.). But the data analysis module 130 can otherwise analyze any suitable dataset or combination of datasets.

The data analysis module 130 preferably determines cardiovascular parameter values of one or more cardiovascular health-related parameters including: arterial stiffness, phase of constriction, pulse transit time, pulse wave velocity, heart rate, heart rate variation, blood pressure, blood pressure variation (e.g., diurnal blood pressure variation), and/or any other suitable cardiovascular parameter type. Cardiovascular parameter values can indicate hypertension, atherosclerosis, narrow of blood vessels, arterial damage, and/or any other suitable cardiovascular risk factor.

The cardiovascular parameter values are preferably associated with a temporal indicator corresponding to the image data from which the cardiovascular parameter value is determined. For example, in relation to a portion of the method 200 described below, a camera module 112 can collect a time series of image data corresponding to a daytime period (e.g., after sunrise and before sunset), the signal generation module can convert the image data into a PPG dataset, the data processing module 120 can process the PPG dataset, and the data analysis module 130 can determine a cardiovascular parameter value from the processed PPG dataset, where the cardiovascular parameter value is associated with the daytime period in which the camera module 112 collected the time series of image data. However, the cardiovascular parameters can additionally or alternatively be associated with any other suitable temporal indicator (e.g., non-daytime period, non-nighttime period, etc.), on any other suitable time scale (e.g., seconds, minutes, hours, days, weeks, months, years, etc.).

3.4 Output Module

As shown in FIG. 1, the output module 140 functions to generate and/or present an analysis of the cardiovascular parameter value to an entity for informing the entity of cardiovascular risk associated with the user. The output module 140 can additionally or alternatively function to automatically facilitate therapy provision to the user based upon an analysis of the cardiovascular parameter value. The output module 140 is preferably implemented at the remote server used in implementing the data processing module 120 and the data analysis module 130, but can be otherwise implemented. The output module 140 preferably includes a communication system configured to transmit the analysis of the cardiovascular parameter value to a user device, a guardian device, a care provider device, and/or any other suitable component. The analysis of the cardiovascular parameter value can be presented at an application executing on a mobile computing device, at a website, as a notification, and/or as any suitable form.

The system 100 can, however, include any other suitable elements configured to receive and/or process data in order to promote assessment or management of cardiovascular health of one or more individuals.

4. Method. As shown in FIGS. 2-3 and 8, an embodiment of a method 200 for assessing cardiovascular disease in a user using a camera module, the method including receiving a time series of image data S210 of a body region of the user, the time series of image data captured during a time period; generating a photoplethysmogram (PPG) dataset from the time series of image data S220; generating a processed PPG dataset S230; determining a cardiovascular parameter value of the user based on the processed PPG dataset S240; fitting a chronobiological model S265 to (1) the cardiovascular parameter value, and (2) a subsequent cardiovascular parameter value; characterizing a cardiovascular parameter variation over time of the user based on the fitted chronobiological model S260; and presenting an analysis of the cardiovascular parameter variation to the user at a mobile computing device S270 associated with the user.

In some variations, the method 200 can additionally or alternatively include implementing an image sampling protocol S280, and automatically facilitating therapy provision S290, thereby promoting cardiovascular health of the user.

In relation to remote assessment of a patient, the method 200 is preferably implemented, at least in part, using a mobile computing device of the patient, such that the patient can be remote from a clinical setting (e.g., hospital, clinic, etc.) during extraction of clinically-relevant parameters associated with cardiovascular disease. As such, the method 200 is preferably implemented, at least in part, at an embodiment, variation, or example of the system 100 described in Section 3 above; however, the method 200 can additionally or alternatively be implemented using any other suitable system(s).

4.1 Receiving Image Data

Block S210 recites: receiving a time series of image data of a body region of the user, the time series of image data captured during a time period. Block S210 functions to acquire data from which relevant cardiovascular health-associated parameters can be extracted and analyzed, according to subsequent blocks of the method 200. Block S210 is preferably implemented at a camera module of a mobile computing device (e.g., a smartphone) associated with the user, but can additionally or alternatively be implemented using any other suitable system component. A time series of image data is preferably received in Block S210, but any type, combination, or number of image data can be received, and processed in future steps, as described in relation to image data types above.

Regarding Block S210, the time series of image data is preferably associated with a time period temporal indicator (e.g., a daytime period, a nighttime period, a sleeping phase, a waking phase, a morning, an afternoon, a night, a sunrise, a sunset, a dawn, a dusk, a twilight, etc.). In a specific example, Block S210 can include: receiving a first time series of image data of the body region of the user, the first time series of image data captured during a daytime period, and the first time series of image data captured at the camera module of the mobile computing device; receiving a second time series of image data of the body region of the user, the second time series of image data captured during a nighttime period, and the second time series of image data captured at the camera module of the mobile computing device. In this specific example, such data can be used to analyze patterns and generate characterizations associated with diurnal variations in one or more cardiovascular health associated parameters; however, variations of Block S210 can alternatively collect any other suitable image data according to any other suitable time scale, and at any other suitable frequency.

With respect to Block S210, the received time series of image data is preferably captured at locations remote from a healthcare provider (e.g., at home, at work, at a social event, etc.), such as to offer a non-invasive, convenient user experience for monitoring, assessment, and treatment of cardiovascular risks. Additionally or alternatively, the received time series of image data can be captured in-clinic (e.g., during a visit to a physician at a hospital), and/or any other suitable location. Captured image data is preferably transmitted to a computing system (e.g., a remote server) with GPU processing capabilities. Pushing data processing to the GPU thus allows the mobile computing device to maximize potential use of camera module functions of the mobile computing device in relation to limitations in processing capacity at the mobile computing device. In variations, the image data is additionally or alternatively transmitted to personal computer modules, mobile computing device modules, cloud-computing modules, and/or any other suitable computing modules for subsequent processing and analysis.

In a first variation of Block S210, receiving a time series of image data can include: providing a user with access to the camera module through an application executing on a mobile computing device associated with a user; automatically prompting, with the application, the mobile computing device to transmit the time series of image data captured by the camera module; and receiving, at a remote server, the time series of image data. In a specific example of this first variation, the application can prompt the user to access the camera module, facilitating user capture of a time series of image data of a specified body region of the user. In response to the user capturing the time series of image data, the application can prompt the internet-enabled mobile computing device to transmit the captured time series of image data to a remote server for further processing and analysis.

Additionally or alternatively, in a second variation of Block S210, receiving a time series of image data can include: providing an interface to the user for manually uploading time series of image data; and receiving the time series of image data through the provided interface. In this variation, the interface can be provided through an application configured to operate on a mobile computing device of the user, through a web interface, or through any other suitable venue. The manually uploaded time series of image data can be captured on the same device performing the upload (e.g., time series of image data captured and uploaded on the same user tablet device), captured on a different device (e.g., image data captured on a digital camera, transferred to a desktop computer, and uploaded through a web interface accessed by the desktop computer), and/or captured on any other suitable component.

Additionally or alternatively, in a third variation of Block S210, Block S210 can be performed in coordination with transmitting light (e.g., from an illumination module of the mobile computing device including the camera module) toward a body region (e.g., a finger placed in the field of view of the camera module) of an individual. The operational states of the camera module and/or the illumination module can be governed at a native application executing at the mobile computing device of the individual to coordinate generation of the data from the individual. In one such specific example, a native application installed at the mobile computing device of the individual can guide the individual in providing PPG data in coordination with transitioning the camera and illumination modules of the mobile computing device into active states. Block S210 can additionally or alternatively include manipulating one or more parameters/operational settings of the hardware components (e.g., the camera module, the illumination module, etc.) implementing Block Silo. For example, Block S210 can include adjusting a focal length of the camera module, adjusting an acquisition rate of the camera module, adjusting a white balance parameter (e.g., tint, temperature) of the camera module of the mobile computing device, and/or manipulating any other suitable camera module function of the mobile computing device. In other examples, with respect to the illumination module, Block S110 can comprise manipulating one or more of: an intensity of emitted light, one or more color parameters (e.g., wavelength, etc.) of emitted light, and any other suitable illumination parameter provided by one or more light sources (e.g., light emitting diodes, LEDs; displays, etc.) of the mobile computing device. However, performing Block S210 in coordination with transmitting light can be conducted in any other suitable manner.

Variations of Block S210 can, however, be performed in any other suitable manner in order to acquire data for processing according to subsequent blocks of the method 200.

4.2 Generating a PPG Dataset

Block S220 recites: generating a photoplethysmogram (PPG) dataset from the time series of image data, which functions to generate PPG signals from image data, for monitoring of perfusion of blood to the dermis and subcutaneous tissue of the skin of the individual, over a duration of time and in a non-clinical setting. Alternative variations of Block S220 can, however, be implemented in association with any other suitable body region of a user, and/or in a clinical setting. The PPG dataset is preferably generated from light absorption data based on image data of a body region of the user, where the light absorption data can provide non-invasive determination of parameters associated with different states of cardiovascular disease. In particular, the PPG dataset is preferably generated from the time series of image data received in Block S210, but can additionally or alternatively be generated form any suitable image data. Generating a PPG dataset S220 is preferably performed for every time series of image data received in Block S210. Additionally or alternatively, a PPG dataset can be generated only for selected time series of image data (e.g., time series of image data of sufficient image quality, time series of image data sufficiently capturing a specific body region of the user within the time series, time series of image data with sufficiently stable motion characteristics, and/or time series of image data with characteristics exceeding any suitable threshold), but a PPG dataset can be generated for datasets selected based on any suitable criteria.

Block S220 is preferably implemented at a signal generation or signal extraction module of a remote server with GPU processing capabilities, but can be otherwise implanted partially or fully at any suitable component. Generating a PPG dataset from the time series of image data is preferably performed in response to receiving the time series of image data (e.g., at a remote server implementing Block S220). Additionally or alternatively, Block S220 can be performed in aggregate, such that Block S220 is performed in response to receiving multiple time series of image data, thereby generating multiple PPG datasets. However, generating the PPG dataset can be performed at any suitable time.

4.3 Generating a Processed PPG Dataset

Block S230 recites: generating a processed PPG dataset, which functions to process the generated raw PPG dataset into a form suitable for specific determination of cardiovascular parameters of the user. Block S230 can additionally or alternatively include: identifying regions of interest S232; filtering with a PPG acquisition model S234; and/or identifying placement error of a body region based on image intensity of the time series of image data S236, as shown in FIG. 2.

Regarding Block S230, generating a processed dataset is preferably performed for a PPG dataset generated in Block S220, thereby generating a processed PPG dataset, but processing as in Block S230 can be performed for any dataset (e.g., a supplementary biosignal dataset), thereby generating supplemental processed datasets. Generating a processed PPG dataset is preferably performed for every PPG dataset generated in Block S230, but can be selectively performed base don any suitable criteria. Generating a processed PPG dataset is preferably performed at a data processing module of a remote server implementing Blocks S210 and S220, but can otherwise be performed partially or fully at any suitable component or combination of components.

With respect to Block S230, generating a processed PPG dataset is preferably performed in response to generating a first PPG dataset in Block S220, but processing can be performed in aggregate on a set of PPG datasets (e.g., multiple PPG datasets generated in Block S220 from multiple received time series of image data corresponding to different time periods). However, generating a processed PPG dataset can be performed at any suitable time on any suitable number or combination of datasets.

For Block S230, generating a processed PPG dataset can include processing a PPG dataset through operations including one or more of: normalization, filtering, noise reduction, smoothing, model fitting, transformations, mathematical operations (e.g., calculating a first derivative of collected signals, positive component squared operations, operations associated with moving averages, etc.), image processing, and/or any other suitable processing technique. Generating processed PPG datasets preferably includes processing each generated PPG dataset using the same or similar processing techniques, such that processed PPG datasets can be compared and/or analyzed in a consistent manner. However, different datasets can be processed through different techniques, different variations of the same techniques, and/or through any suitable manner.

4.3.A Identifying Regions of Interest

Figure 4:
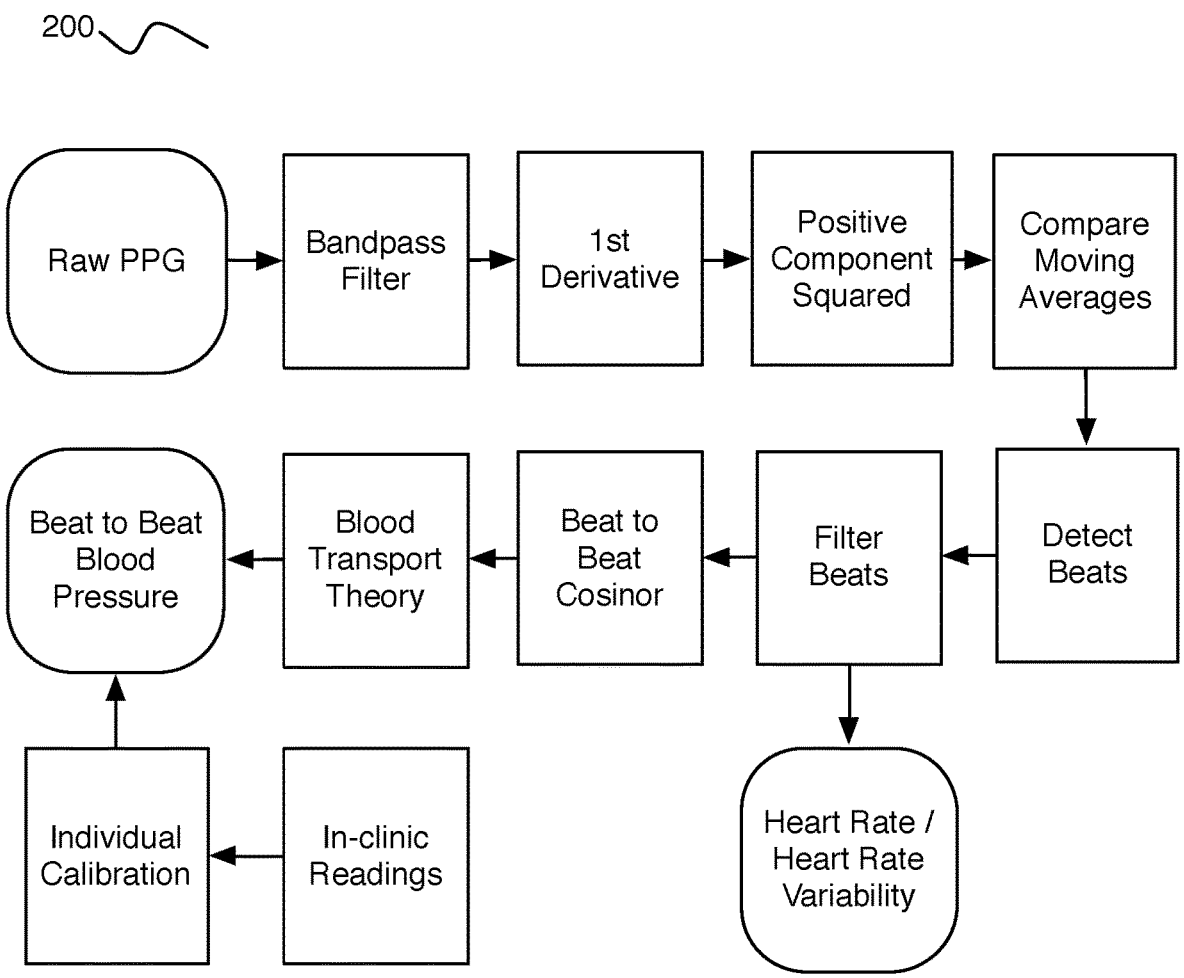
FIG. 4 depicts an application flow of an embodiment of a method for monitoring and assessing cardiovascular disease.
Figure 5:
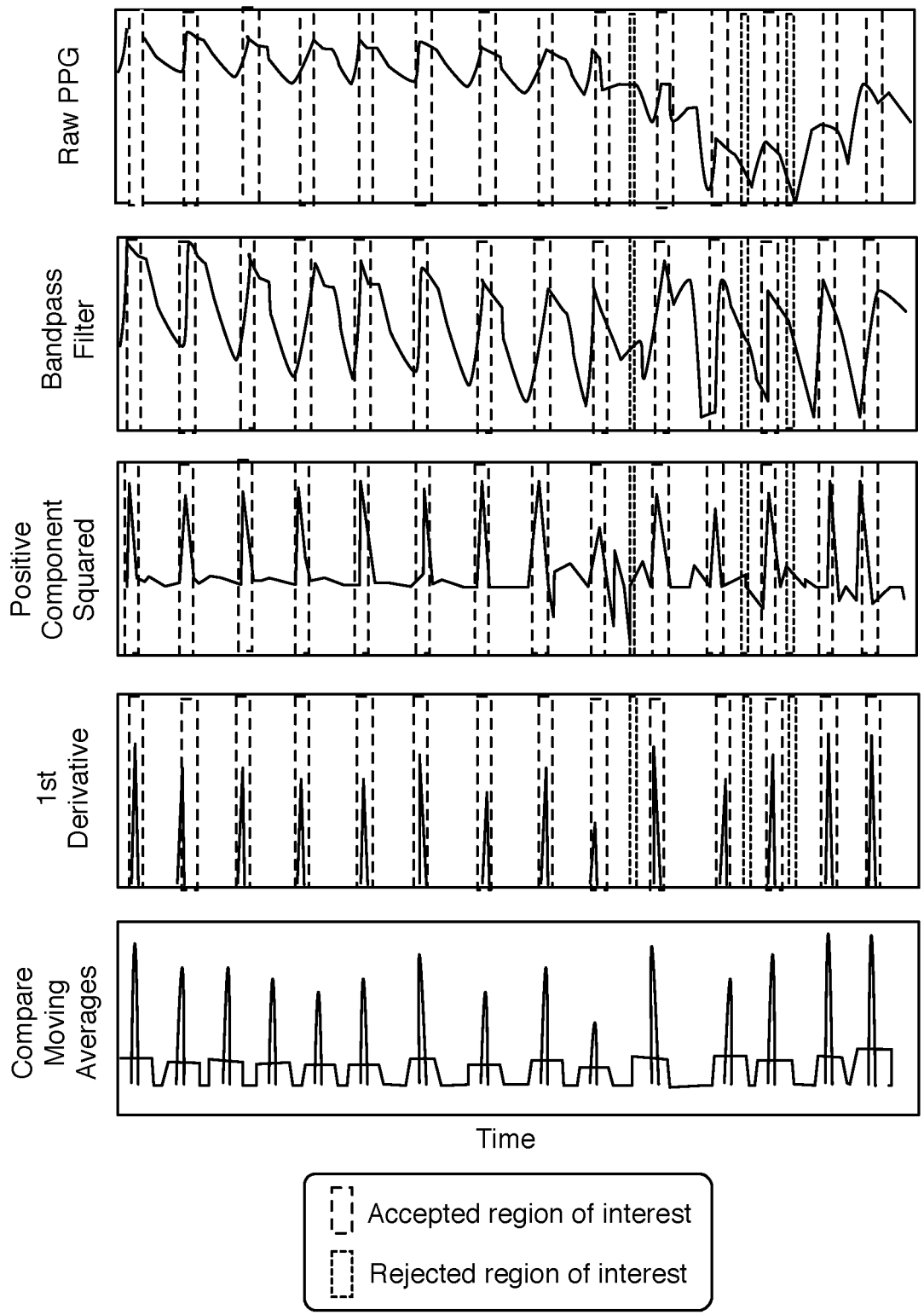
FIG. 5 depicts an example of processing a PPG dataset in a portion of a method for monitoring and assessing cardiovascular disease.

In a first variation of Block S230, as shown in FIGS. 4-5, generating the processed dataset can additionally or alternatively include identifying regions of interest S232, which functions to filter the PPG dataset for regions of interest to perform subsequent processing and/or analysis steps upon. Identifying regions of interest preferably includes the processing steps of: bandpass filtering, performing a first derivative dataset, calculating a positive component squared, and comparing a moving average dataset across the positive component squared dataset, but can additionally or alternatively include any suitable processing step performed on any suitable dataset. Identifying regions of interest is preferably based on the comparison of the moving average dataset across the positive component squared dataset, thereby identifying heartbeat regions of interest. In a specific example, the short and long moving averages from the PPG dataset are compared across the positive component squared of the first derivative dataset of the bandpass filtered PPG dataset generated in Block S220. Identified heartbeat regions of interest are preferably filtered through criteria including: length of region, amplitude of positive component, time since previous beat, and/or any other suitable criteria.

In a specific example of Block S232, identifying heartbeat regions of interest can include: generating a moving average dataset in near real-time based on the PPG dataset, wherein the processed PPG dataset is further based on the moving average dataset. In this specific example, the Block S232 can further include: filtering the PPG dataset with a bandpass filter; deriving a first derivative dataset from the bandpass filtered PPG dataset; generating a positive component squared dataset from the first derivative dataset; and generating a comparison of the moving average dataset across the positive component squared dataset, wherein generating the processed dataset S230 is based on the comparison. Additionally, Block S232 can include: identifying heartbeat regions of interests based on the comparison of the moving average dataset across the positive component squared dataset; and filtering the heartbeat regions of interest based on at least one of: length of region, amplitude of positive component, and time since previous beat, wherein generating the processed PPG dataset S230 is based on the filtered heartbeat regions of interest. However, identifying regions of interest can be performed in any other suitable manner.

4.3.B Filtering with a PPG Acquisition Model

In a second variation of Block S230, as shown in FIG. 2, generating the processed dataset can additionally or alternatively include filtering with a PPG acquisition model S234. Filtering with a PPG acquisition model can be performed on a dataset generated in Block S220, S230, S232, S236, and/or any other suitable dataset. Filtering with a PPG acquisition model S234 preferably includes: generating a PPG acquisition model from historical PPG dataset; and filtering the PPG dataset with the PPG acquisition model generated from the historical PPG data, wherein generating the processed PPG dataset is based on the filtered PPG dataset, and wherein the processed PPG dataset is a subset of the PPG dataset. Filtering with the PPG acquisition model can be based on user information (e.g., demographic information, user-inputted data, etc.), collected data (e.g. collected supplemental sensor data, image data, etc.), care provider information, predetermined criteria (e.g., manually selected PPG data characteristics, manual labeling of training data for a machine learning model, etc.), automatically determined criteria (e.g., using a machine learning model, etc.), and/or any other suitable criteria. The PPG acquisition model can include probabilistic properties, heuristic properties, deterministic properties, and/or any other suitable properties for filtering PPG datasets. PPG signals, signal regions, and/or any suitable portion of PPG datasets are preferably classified with a "valid" classification or a "compromised" classification, but can otherwise be classified.

In a specific example of Block S234, Block S234 can include: classifying historical PPG signals as compromised historical PPG signals or valid historical PPG signals; generating the PPG acquisition model based on the classified historical PPG signals; and filtering a PPG dataset using the PPG acquisition model, based on feature similarity of the PPG signals with the compromised historical PPG signals and the valid historical PPG signals, wherein generating the processed PPG dataset is based on the filtered PPG dataset. However, filtering with a PPG acquisition model S234 can be performed in any other suitable manner.

4.3.C Identifying Placement Error Based on Image Intensity

In a second variation of Block S230, as shown in FIG. 2, generating the processed dataset can additionally or alternatively include identifying placement error of a body region of a user, based on image intensity S236, which functions to identify and correct for user error in capturing a body region of the user with a camera module. Identifying placement error is preferably performed for identifying a finger placement error of the user, but a placement error can be identified for any suitable body region of the user. Identifying body region placement error is preferably based on image intensity characteristics (e.g., a two-dimensional distribution of intensity variation) of a time series of image data received as in Block S210, but can be based on any suitable image data property. Body region placement errors can be corrected through normalization based on the identified placement errors. Placement error identification and/or normalization can be performed across a single time series of image data, multiple time series of image data, and/or any suitable granularity of image data.

In a specific example of Block S230, the body region is a finger of the user, the body region of the user is a finger of the user, where generating the processed PPG dataset comprises: identifying a placement error of the finger based on two-dimensional distribution of intensity variation of the time series of image data (e.g. a time series of image data received as in Block S210); correcting the PPG dataset based on the placement error of the finger; and generating the processed PPG dataset based on the corrected PPG dataset. In other examples, Block S230 can additionally or alternatively include correcting for variations in motion and/or fingertip pressure based on observations of the imaging frame data in time. However, Block S236 can be performed in any other suitable manner.

4.4 Determining a Cardiovascular Parameter Value

Block S240 recites: determining a cardiovascular parameter value of the user based on the processed PPG dataset, which functions to determine a cardiovascular parameter value indicative of a cardiovascular risk associated with the user. Block S240 can additionally or alternatively include fitting a cosinor model to a dataset S250, and characterizing a cardiovascular parameter variation over time S260.

With respect to Block S240, types of cardiovascular parameter values that can be determined in Block S240 include one or more of: arterial stiffness, phase of constriction, pulse transit time, pulse wave velocity, heart rate, heart rate variation, blood pressure, blood pressure variation (e.g., diurnal blood pressure variation), and/or any other suitable cardiovascular parameter types. Cardiovascular parameter values can indicate hypertension, atherosclerosis, narrow of blood vessels, arterial damage, and/or any other cardiovascular risk factor.

Regarding Block S240, determining a cardiovascular parameter value is preferably in response to generating a processed dataset S230, but can have any suitable temporal relationship with any other portion of the method 200.

In relation to Block S240, A cardiovascular parameter value is preferably determined from analyzing a processed PPG dataset, but can additionally or alternatively be determined based on a raw PPG dataset, a supplementary dataset, and/or any other suitable dataset (e.g., a dataset from Blocks S210, S220, S230, S232, S234, and/or S236). Additionally or alternatively, cardiovascular parameters can be determined without using specific types of data. For example, determining a cardiovascular parameter value can be based on datasets of only the PPG data type. In another example, cardiovascular parameter values can be determined without using electrocardiogram (ECG) data. In a specific example, determining the blood pressure parameter value of the user includes determining the blood pressure parameter value without using ECG signals, and wherein characterizing a diurnal blood pressure variation of the user comprises characterizing a diurnal blood pressure variation without using ECG signals. Determining a cardiovascular parameter value can include determining the cardiovascular parameter using models and/or approaches possessing probabilities properties, heuristic properties, deterministic properties, and/or any other suitable feature for calculating cardiovascular parameter values from a processed PPG dataset and/or any suitable dataset. However, cardiovascular parameter values can be determined in any suitable manner.

Figure 6:
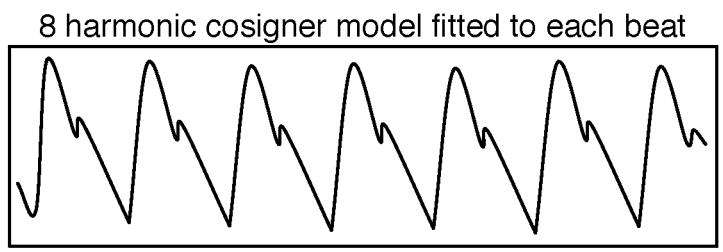
FIG. 6 depicts an example of fitting a harmonic cosinor model in a portion of a method for monitoring and assessing cardiovascular disease.

Regarding Block S240, as shown in FIG. 6, determining a cardiovascular parameter value can additionally or alternatively include fitting a cosinor model to a dataset S250. A cosinor model is preferably fitted to a processed PPG dataset as in Block S230, but can be fitted to any suitable dataset or combination of datasets. For example, Block S240 can include fitting harmonic cosinor model to the processed PPG dataset, wherein determining the cardiovascular parameter value comprises determining the cardiovascular parameter based on the fitted harmonic cosinor model. In specific examples (e.g., examples in which the pulse waveform of the target dataset has a harmonic structure), the phase and amplitude of harmonic components of the waveform can be estimated per beat using:

$$Y(t) = A_0 + \sum_n A_n \cos\left(\frac{2\pi n t}{T} + \phi_n\right) + \varepsilon$$

where T is the length of the beat.

Regarding Block S250, fitting a cosinor model to the dataset is preferably based on a time window (e.g., a continuous 24 hour time window including a daytime period and a nighttime period) associated the dataset, but can additionally or alternatively be based on any suitable temporal indicator. For example, fitting the cosinor model to the dataset can include selecting a particular cosinor model and/or parameters of a cosinor model based on the time window associated with the dataset upon which the cosinor model will be fitted. However, fitting a cosinor model to a dataset can be performed in any other suitable manner.

Block S240 can additionally or alternatively include characterizing a cardiovascular parameter variation over time S260. Determining cardiovascular parameter variation S260 is preferably performed for blood pressure (e.g., characterizing a diurnal blood pressure variability), but can be performed for any suitable cardiovascular parameter. Diurnal cardiovascular parameter variation (e.g., variation throughout a day) can be characterized in Block S260. Additionally or alternatively, any other suitable cardiovascular parameter variation can be characterized over any suitable temporal indicator in variations of Block S260. In a specific example, a fitted chronobiological model a set of cardiovascular parameters sharing a cardiovascular parameter type, the set of cardiovascular parameters corresponding to a time window comprising a time period (e.g., a daytime period), a second time period (e.g., a nighttime period), and a continuous 24 hour time period, wherein characterizing the cardiovascular parameter variation over time comprises characterizing the cardiovascular parameter variation over the time window. However, characterizing the cardiovascular parameter variation over time can be otherwise performed.

Figure 7A:
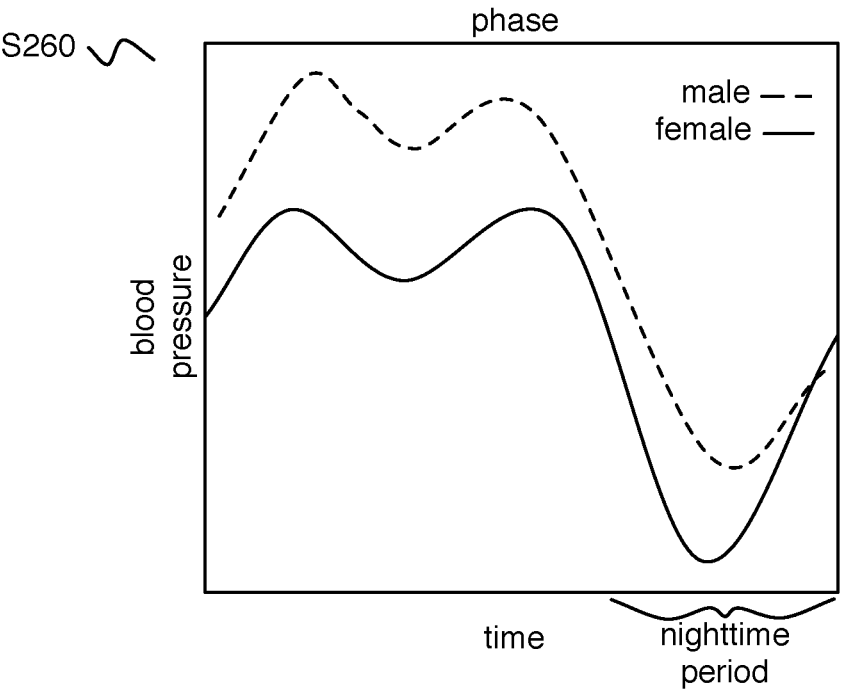
FIGS. 7A-7B depict examples of fitting chronobiological models in a portion of a method for monitoring and assessing cardiovascular disease.
Figure 7B:
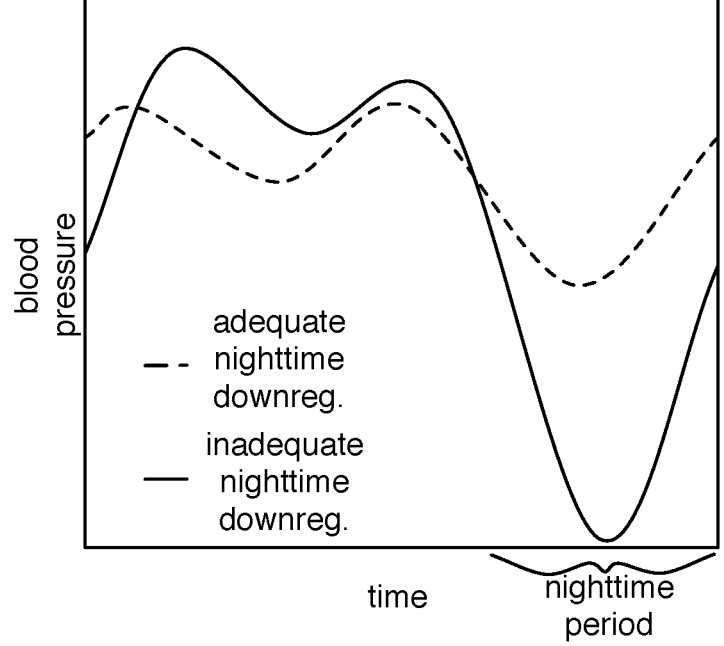

Regarding Block S260, as shown in FIGS. 7A-7B, characterizing cardiovascular parameter variation over time can include fitting a chronobiological model to a set of cardiovascular parameter values S265. The set of cardiovascular parameter values preferably includes one or more cardiovascular parameter values determined as in Block S240, but can additionally or alternatively include any suitable cardiovascular parameter value. In a specific example, Block S260 can include fitting a chronobiological model to (1) the cardiovascular parameter value associated with the first time period, and (2) a subsequent cardiovascular parameter value associated with a second time period, wherein the cardiovascular parameter value and the subsequent cardiovascular parameter value share a cardiovascular parameter type, wherein characterizing a first cardiovascular parameter variation over time is based on the fitted first chronobiological model. However, fitting a chronobiological model to a set of cardiovascular parameter values S265 can be performed in any suitable manner.

With respect to Block S260, fitting the chronobiological model preferably enables extrapolation of cardiovascular parameter values corresponding to time points (or other temporal indicators) at which cardiovascular parameter values were not generated. For example, for a continuous 24 hour period, a user may capture five time series of image data, corresponding to 8 AM, 12 PM, 4 PM, 8 PM, and 12 AM. Cardiovascular parameter values can be determined for each of the five time series of image data, and Block S260 can include: in response to fitting a chronobiological model to the cardiovascular parameter values, extrapolating cardiovascular parameter values corresponding to time points without overlap with the time points (or other temporal indicators) corresponding to the captured time series of image data (e.g., not corresponding to 8 AM, 12 PM, 4 PM, 8 PM or 12 AM). However, extrapolating cardiovascular parameter values based on a fitted chronobiological model can be performed in any suitable manner.

4.4.A Determining a Cardiovascular Parameter Value—Specific Variations

In a first variation of Block S240, as shown in FIG. 4, determining a cardiovascular parameter value can include determining a heart rate value of the user. The heart rate value is preferably determined from a PPG dataset processed as in Block S232. For example, the heart rate value is preferably determined from a PPG dataset processed by: filtering the PPG dataset with a bandpass filter; deriving a first derivative dataset from the bandpass filtered PPG dataset; generating a positive component squared dataset from the first derivative dataset; generating a comparison of the moving average dataset across the positive component squared dataset to identify regions of interest (e.g., heartbeat regions of interest); and filtering the heartbeat regions of interest based on criteria including at least one of length of region, amplitude of positive component, and time since previous beat. Additionally or alternatively, determining the heart rate value can be based on any suitable dataset processed in any suitable manner. The heart rate value is preferably derived from the peak-to-peak interval of the processed PPG dataset, where minima, maxima, and/or any suitable feature or interval can be identified. However, heart rate values can be determined with any other suitable approach.

Additionally or alternatively, in a second variation of Block S240, as shown in FIG. 4, determining a cardiovascular parameter value can include determining a heart rate variability based on the heart rate value of the user. Determining the heart rate variability is preferably based on a set of heart rate values determined as in the first specific variation of Block S240. However, heart rate variability can be determined in any suitable manner.

Additionally or alternatively, in a third variation of Block S240, as shown in FIG. 4, determining a cardiovascular parameter value can include determining a blood pressure parameter value for the user. A determined blood pressure parameter value is preferably associated with one of a daytime period and a nighttime period (e.g., to facilitate analysis of diurnal blood pressure variability), but can be associated with any suitable temporal indicator.

In the third variation of Block S240, determining the blood pressure parameter value preferably includes fitting a cosinor model (e.g., a harmonic cosinor model) to a PPG dataset processed as in Block S230; and determining the blood pressure value of the user based on the fitted cosinor model. In examples, the phase and amplitude of harmonic components can be estimated from the fitted cosinor model, and in an example, such parameters can be used in determining the blood pressure parameter value through blood pressure transport theory:

$$DBP = c_{0,0}A_0 + c_{4,0}A_4$$

$$PP = c_{1,1}A_1$$

$$SBP = DBP + PP$$

where DBP is diastolic blood pressure, SBP is systolic blood pressure, PP is pulse pressure, $A_n$ are harmonic components, and $c_{n,n}$ are constants. In a specific example, determining the blood pressure parameter value can include: determining an amplitude of a harmonic component of the fitted cosinor model; and determining the blood pressure parameter value based on the amplitude of the harmonic component. In such examples, model coefficients can be estimated through calibration datasets (e.g., calibration PPG and calibration blood pressure datasets measured, for example, in-clinic during user on-boarding with an embodiment of the method 200).

As an illustration, the determining the blood pressure parameter value can include receiving a calibration PPG dataset corresponding to a time period; receiving a calibration blood pressure dataset corresponding to the time period; and determining the blood pressure parameter value based on the calibration PPG dataset, the calibration blood pressure dataset, and an amplitude of the harmonic component of a fitted cosinor model. However, determining the blood pressure parameter value can be otherwise determined.

Additionally or alternatively, in a fourth variation of Block S240, as shown in FIGS. 4 and 7A-7B, determining a cardiovascular parameter value can include characterizing a blood pressure variability over time. A diurnal blood pressure variability (e.g., blood pressure variability throughout the day) is preferably determined, but blood pressure variability can be determined across and/or associated with any suitable temporal indicator. Blood pressure variability over time is preferably characterized based upon a set of blood pressure parameter values determined as in the third specific variation of Block S240. Additionally or alternatively, blood pressure variability can be determined based on blood pressures determined from a supplemental sensor, from third-party sources (e.g., public databases, private health records, third-party medical devices, user-inputted blood pressures, etc.), and/or any other suitable source.

In the fourth variation of Block S240, determining the cardiovascular parameter value can include fitting a chronobiological blood pressure model to a set of blood pressure parameter values. The set of blood pressure parameter values preferably includes one or more blood pressure parameter values determined as in the third specific variation of Block S240. For example, characterizing a diurnal blood pressure variation of the user can be based on the fitted chronobiological blood pressure model. In a specific example, characterizing diurnal blood pressure variation includes fitting a chronobiological blood pressure model to (1) a blood pressure parameter value associated with the daytime period and (2) a blood pressure parameter value associated with the nighttime period. In specific examples, the rhythmic change in blood pressure during the course of a day can be described with a sum of cosines:

$$y_n = M + \sum_{c=1}^{C} A_c \cos(\omega_c t_n + \phi_c) + e_n; n = 1, \ldots, N,$$

where $y_n$ is the observed blood pressure value at time $t_n$; C is the number of sinusoidal components (e.g., C=2); and $\omega_c$ are the diurnal angular frequencies for each sinusoidal component; $\phi_c$ is the angular phase (offset) of each angular frequency; and N is the number of observation samples. Angular frequencies can be any suitable time period (e.g., 1 hour period, 24 hour period, etc.). In such specific examples, parameters can be estimated with least squares minimization of the residual sum of squares (RSS) of the observed blood pressure measures against modeled blood pressure:

$$RSS(M, A_1, t, \phi_1, \ldots, t_c, \phi_c) = \sum_{n=1}^{N} e_n^2 = \sum_{n=1}^{N} (y_n^{obs} - y_n^{est})^2,$$

where solving the system can provide a vector of parameters:

$$\theta = (\hat{M}, \widehat{A_1}, \widehat{t_1}, \widehat{\phi_1}, \ldots, \widehat{t_c}, \widehat{\phi_c})$$

In the fourth variation, characterizing the diurnal blood pressure variation can include characterizing the diurnal blood pressure variation based upon analysis of the fitted chronobiological blood pressure model. For example, determining a blood pressure variability can include: identifying a nighttime region of the fitted chronobiological blood pressure model; the nighttime region associated with a nighttime period; determining a degree of blood pressure dip at the nighttime region; and characterizing the diurnal blood pressure variation based on the degree of blood pressure dip at the nighttime region. In a specific application, a lack of blood pressure dip at the nighttime region of a fitted chronobiological blood pressure model can indicate an inability to appropriately downregulate blood pressure during nighttime, which can indicate cardiovascular risk and provide guidance for appropriate treatments. However, fitting the chronobiological blood pressure model can be performed in any suitable fashion.

4.5 Presenting an Analysis

Block S270 recites: presenting an analysis of the cardiovascular parameter variation to the user at the mobile computing device, which functions to generate and/or present an analysis of one or more cardiovascular parameter values to an entity for informing the entity of cardiovascular risk associated with the user. A remote server (e.g., a remote server implementing other Blocks of the method 200) preferably transmits a generated analysis (e.g., also generated at the remote server) to a mobile computing system associated with a user, care provider, guardian, and/or any other suitable entity. In a specific example, presenting an analysis includes presenting an analysis of a cardiovascular parameter variation to a user at a mobile computing device associated with the user. In another specific example, the analysis of a cardiovascular parameter can be transmitted to a mobile computing device comprising a camera module used in capturing a received time series of image data from which the cardiovascular parameter was determined. However, any suitable component can transmit, receive, and/or present any suitable analysis of a cardiovascular parameter.

Regarding Block S270, presenting an analysis preferably includes presenting an analysis of a cardiovascular parameter variation over time as determined in Block S260, but an analysis of any suitable cardiovascular parameter can be presented. The presented analysis can be generated based on one or more fitted models, cardiovascular parameters, and/or any other suitable data. For example, generating an analysis of cardiovascular parameter variation can include presenting and/or comparing variations in multiple different cardiovascular parameters over time.

Additionally or alternatively, in specific examples, presenting an analysis can include comparing cardiovascular parameter variations over time of multiple users. In a specific examiner where a first chronobiological model has been fitted to cardiovascular parameters associated with first user and associated with a first and a second time period within a first time window, presenting the analysis S270 can include: fitting a second chronobiological model to (1) cardiovascular parameter associated with a second user and associated with a third time period, and (2) a subsequent cardiovascular parameter associated with the second user and associated with a fourth time period, the third and the fourth time periods within a second time window; characterizing a second cardiovascular parameter variation over time of the second user based on the fitted second chronobiological model; and generating a comparison between the first cardiovascular parameter variation over time (e.g., based on the first chronobiological model fitted to cardiovascular parameters associated with the first and the second time period) and the second cardiovascular parameter variation over time, wherein the analysis of the cardiovascular parameter is based on the comparison.

Additionally or alternatively, in specific examples, presenting an analysis can include generating an analysis based on multiple cardiovascular parameters (e.g., cardiovascular parameters of the same type but associated with different temporal indicators, cardiovascular parameters of different types, etc.) determined for a user. In a specific example, presenting an analysis 270 can include: characterizing a diurnal heart rate variation of the user; characterizing a diurnal blood pressure variation of the user based on a fitted chronobiological mode; generating an analysis based on the diurnal heart rate variation and the diurnal blood pressure variation; presenting the analysis to the user; and automatically facilitating therapy provision to the user based upon the analysis.

With respect to Block S270, the analysis can be any number or combination of forms, including numerical (e.g., cardiovascular parameter values, cardiovascular risk values, probabilities, raw values, processed values, etc.), verbal (e.g., verbal indications of cardiovascular risk and/or disease, recommendations, etc.), graphical (e.g., colors indicating risk state, educational graphics, etc.), and/or any suitable form.

In relation to Block S270, presenting the analysis can include presenting the analysis based on rules (e.g., notification preferences set by a user, rules established by a care provider, by a guardian, etc.), time (e.g., notification at set frequencies, times of day, etc.), steps (e.g., presenting an analysis in response to generating the analysis, which can be in response to characterizing cardiovascular parameter variation), and/or any other suitable criteria.

In a first variation of Block S270, presenting an analysis can include automatically notifying an entity through an application executing on a corresponding mobile computing device. Automatic notifications can be transmitted from a remote server to a mobile computing device associated with a user, a guardian, a care provider, and/or any other suitable entity. Automatic notifications can take the form of a native application notification, a text message, a web interface, an application interface, and/or any other suitable form. Automatically notifying an entity is preferably in response to generating an analysis of a cardiovascular parameter, but can be performed at any suitable time in relation to any suitable portion of the method 200. However, automatically notifying an entity can be performed in any suitable manner In a second variation of Block S270, presenting an analysis can include automatically presenting an alert in response to a characteristic of the analysis of the cardiovascular parameter exceeding a threshold. Thresholds can be established (e.g., by a care provider, by a guardian, by a user, by a third party, etc.) for characteristics of any suitable model, dataset, cardiovascular parameter, cardiovascular parameter variation, and/or any suitable component of the method 200. For example, presenting an analysis of diurnal blood pressure variation can include presenting a warning to the user at the mobile computing device in response to the degree of blood pressure dip less than a threshold degree at a nighttime region of a fitted chronobiological blood pressure model. In another example, presenting an analysis of heart rate variability can include presenting a warning to a care provider at a care provider mobile computing device in response to the heart rate variability exceeding a heart rate variability threshold. However, presenting an alert based on thresholds can be performed in any suitable manner.

4.6 Implementing an Image Sampling Protocol

Block S280 recites: implementing an image sampling protocol, which functions to determine a timing and frequency for prompting the user to perform an image sampling process to collect image data in characterizing cardiovascular parameters. Implementing an image sampling protocol can additionally or alternatively include: receiving user information associated with a user; generating an image sampling protocol for the user; and providing a notification to the user prompting to the user to capture image data with a camera module, based on the image sampling protocol. Implementing sampling protocols can facilitate improved specificity, user adherence, user experience, and/or other various aspects of the method 200. Implementing an image sampling protocol is preferably performed at a remote server (e.g., the remote server receives user information; generates an image sampling protocol based on user information; and transmits an alert to a user prompting image data capture, based on the generated image sampling protocol), but can be implemented partially or fully at any suitable component.

Regarding Block S280, implementing an image sampling protocol preferably includes receiving user information associated with a user. User information can be received from a user, a care provider, a guardian, a third party (e.g., a public database), and/or any other suitable entity. Receiving user information can include receiving user information through an application executing on a mobile computing device, a web interface, non-digitally, and/or through any other suitable means. Types of user information can include: user account information, user profile information, user health records, user demographic information, associated care provider information, associated guardian information, user device information (e.g., GPS location, battery state of charge, calendar information, sensor information, etc.), user schedule information (e.g., is the user currently busy, etc.), time of day, sleep patterns (e.g., sleep phase), waking patterns, degree of physical activity, current biosignal status (e.g., current heart rate, current brain activity, etc.), supplemental sensor information, guardian-provided information for the user, care provider-provided information for the user, and/or any other suitable type of user information. However, receiving user information can otherwise be performed.

In relation to Block S280, implementing an image sampling protocol preferably includes generating and/or optimizing an image sampling protocol for the user. An image sampling protocol can be configured to specify parameters for frequency (e.g., how often to prompt a user), timing (e.g., at what time during the day to prompt the user), notification format (e.g., text message, push notification, application notification, desktop reminder, etc.), transmission mode (e.g., wireless transmission, through a web interface, through an application, etc.), destination (e.g., notifying at a user mobile computing device, at a guardian mobile computing device, etc.), and/or any suitable characteristic with respect to sampling. Generating an image sampling protocol is preferably based on received user information, and can additionally or alternatively be based on models, datasets, cardiovascular parameters, population data, public databases, simulated data (e.g., underlying model noise) and/or any other suitable information related to portions of the method 200. In one example, Block S280 can include receiving sleep phase information (e.g., through an application executing on the mobile computing device, through an external medical device, etc.) of the user, wherein optimizing the image sampling protocol comprises optimizing the image sampling protocol based on the sleep phase information. In another example, the predetermined timing for prompting a user to capture a second time series of image data can be updated based on the actual timing of when a user captured a first time series of image data. However, any suitable information can be used in generating and/or optimizing an image sampling protocol for the user.

In a specific example, Block S280 can include updating a sampling protocol in response to a user recording a time series of image data leading to a faulty PPG dataset, and/or in response to a user recording a time series of image data outside a threshold time window determined by the optimal sampling protocol. Additionally or alternatively, sampling protocols can be generated and/or optimized in relation to parameters imposed by one or more target cardiovascular parameters to be determined. For example, specific types of simulated data and/or user information can be used and/or weighted differently in response to a target goal of determining diurnal blood pressure variation rather than determining heart rate variability. Further, One or more image sampling protocols for one or more users can be generated and/or optimized using models (e.g., machine learning models, Bayesian networks, deep learning models, etc.), and/or approaches possessing probabilistic properties, heuristic properties, deterministic properties, and/or any other suitable properties. However, generating and/or optimizing an image sampling protocol can be performed in any suitable manner.

With respect to Block S280, implementing an image sampling protocol preferably includes a providing a notification to the user that prompts the user to capture image data, based on the image sampling protocol. Providing a notification can additionally or alternatively include providing guidance (e.g., orienting the mobile computing device, directions on how to operate the mobile computing device, etc.) to the user to control the mobile computing device to illuminate a body region and/or capture image data. The notification is preferably provided at the device (e.g., a smartphone) including the camera module, but can be provided at any suitable device associated with the user. Additionally or alternatively, providing a notification can be performed in any manner analogous to presenting an analysis S270. In a specific example, presenting a notification to the user includes: before receiving a time series of image data, presenting, based on the optimized image sampling protocol, a notification to the user at the mobile computing device at a notification time period, the notification prompting the first user to capture the time series of image data at the camera module of the mobile computing device. Block S280 can additionally or alternatively include adjusting for low user adherence. For example, Block S280 can include updating a sampling protocol and/or correcting a dataset for time discrepancies between a provided notification and the actual time a user captures a time series of image data. However, providing a notification to the user can be performed in any suitable manner.

4.7 Automatically Facilitating Therapy Provision

Block S290 recites: automatically facilitating therapy provision to the user, which functions to apply a therapy to the user based on a portion of the method 200, as shown in FIG. 8. Automatically facilitating therapy provision to the user is preferably based upon an analysis of a cardiovascular parameter as in Block S270, but can be based on any suitable model, dataset, cardiovascular parameter, supplemental data (e.g., public data), and/or any suitable information. In a specific example, the method 200 can include: generating a moving average dataset in near real-time based on the PPG dataset, wherein the processed PPG dataset is further based on the moving average dataset, and automatically facilitating therapy provision to the user based upon the analysis in near real-time. Automatically facilitating therapy provision to the user S290 can include one or more of: automatically modulating medication provision, automatically adjusting an environmental aspect of the user, providing a medical recommendation, facilitating telemedicine digital communications between a user and another entity, and/or any suitable therapy approach. Block S290 Is preferably partially or fully implanted at a remote server (e.g., a remote server implementing other Blocks of the method, but can be implemented at any suitable component). In variations, automatically facilitating therapy provision can include transmitting instructions to a mobile computing device, the instructions prompting the mobile computing device to instruct a secondary mobile computing device to apply the therapy. In a specific example, Block S290 can include generating, at a remote server, instructions for automatically adjusting an environmental aspect of the user; transmitting the instructions to a mobile computing device (e.g., a smartphone connected to a home network of the user) the instructions prompting the mobile computing device to wirelessly communicate with a secondary device to adjust the environmental aspect (e.g., a television connected to the home network of the user). However, automatically facilitating therapy provision can be performed in any suitable manner.

In a first variation of Block S290, automatically facilitating therapy provision can include automatically modulating medication provision. Characteristics of medication provision that can be modulated include: dosage level, dosage frequency, type of medication, medication regimen, medication information, prescription renewal, prescription retrieval, and/or any other suitable medication provision characteristic. Modulation of medication provision can include providing notifications regarding the modulation (e.g., providing a notification to take a blood pressure medication based on a characterized diurnal blood pressure variation as in Block S260 and/or Block S270), automatically communicating with another entity (e.g., renewing a prescription with a pharmacy, contacting a care provider regarding the medication, etc.), and/or any suitable action. Automatically facilitating therapy provision can be implemented using automatic medication dispensing apparatus (e.g., a wirelessly-connected medication dispenser), such that this variation of Block S290 includes providing commands from the computing system to the medication dispenser based upon analyses outputted from previous blocks of the method 200. However, automatically modulating medication provision can be performed in any suitable manner.

Additionally or alternatively, in a second variation of Block S290, automatically facilitating therapy provision can include automatically adjusting an environmental aspect of the user. Adjusting an environmental aspect can include: selecting an environmental aspect to adjust from at least one of lighting audio, and temperature; determining a degree of adjustment (e.g., how much lighting, audio, or temperature to adjust), a timing of adjustment (e.g., automatically adjusting in response to generating an analysis of a cardiovascular parameter, scheduling an adjustment for a particular time or frequency, etc.), and/or any suitable characteristic. A lighting environmental aspect can be the lighting of a mobile computing device of the user (e.g., the mobile computing device used in capturing the time series of image data from which a cardiovascular parameter is determined), a connected lightbulb (e.g., a smart lightbulb connected on the same network as a smartphone of a user), and/or any other suitable lighting component. An audio environmental aspect can be an audio of a mobile computing device (e.g., automatically controlling a mobile computing device to play a selected audio tone or musical sample, modifying the volume setting of a mobile computing device, etc.), a connected audio output device (e.g., a speaker, a television, a secondary mobile computing device, etc.), and/or any suitable device. A temperature environmental aspect can be controlled through a temperature control device (e.g., a connected thermometer, a connected air conditioning and/or heating system, etc.). However, environmental aspects can possess any suitable characteristic, and adjusting an environmental aspect can be performed in any suitable manner.

Additionally or alternatively, in a third variation of Block S290, automatically facilitating therapy provision can include providing a medical recommendation. A medical recommendation can be provided to one or more of: a user (e.g., for the user to implement themselves), a care provider, a guardian, and/or any suitable entity. A medical recommendation can include a recommendation to perform a specific action (e.g., to take a walk, to rest, to think positive thoughts, etc.), to stop performing a specific action, to take a medication, to communicate with other entity, and/or any suitable activity. The medical recommendation is preferably provided at the mobile computing device associated with the entity to be notified, but can be provided at any suitable device.

Additionally or alternatively, in a fourth variation of Block S290, automatically facilitating therapy provision can include facilitating a digital communication between a user and another entity. A digital communication is preferably enabled between a user and a care provider, but can be enabled between a user and a guardian and/or any relevant entity. A digital communication is preferably enabled through an application (e.g., a phone calling application, a text messaging application, an application implementing portions of the method 200, etc.), executing on a mobile computing device associated with a user, but such digital communication can be facilitated through any suitable venue. Facilitating a digital communication between a user and another entity can include: providing an analysis of a cardiovascular parameter to one or more of the user and the other entity, guiding the user and/or the other entity through review of the analysis and/or generation of a treatment based on the analysis, and/or any suitable action. However, automatically facilitating therapy provision can be performed in any other suitable manner.

Embodiments of the method 200 can, however, include any other suitable blocks or steps configured to control, modulate, or process information derived from one or more of: hardware aspects of the data acquisition system(s) implementing the method; user experience/user interface (UX/UI) aspects of the system(s) implementing the method; population specific data; sampling site variability; and other suitable sources in order to generate high quality data for characterization, assessment, and management of cardiovascular disease.

Variations of the method 200 and system 100 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and/or one or more portions of a control module and a processor. The computer-readable medium can be stored on any suitable computer readable media such as RAMs, ROMs, flash memory, EEPROMs, optical devices (CD or DVD), hard drives, floppy drives, or any suitable device.

The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method comprising:
for each of a first and second time period:
receiving a time series of data of a body region of a user, the time series of data associated with the respective time period;
generating a photoplethysmogram (PPG) dataset from the time series of data; and
determining a cardiovascular parameter value of the user based on the PPG dataset, the cardiovascular parameter value associated with the respective time period; and
using a chronobiological model, determining a cardiovascular metric based on (1) the cardiovascular parameter value associated with the first time period, and (2) the cardiovascular parameter value associated with the second time period.

2. The method of claim 1, wherein determining the cardiovascular metric comprises fitting the chronobiological model to (1) the cardiovascular parameter value associated with the first time period, and (2) the cardiovascular parameter value associated with the second time period.

3. The method of claim 1, wherein the cardiovascular metric is based on a cardiovascular parameter variation over time.

4. The method of claim 1, wherein the time series of data is a time series of image data sampled using a camera of a mobile device.

5. The method of claim 1, further comprising determining an analysis of the cardiovascular metric, wherein the analysis of the cardiovascular metric is based on a comparison between the cardiovascular metric of the user and a second cardiovascular metric associated with a second user.

6. The method of claim 1, further comprising:
identifying a cardiovascular risk level based on the cardiovascular metric; and when the cardiovascular risk level exceeds a threshold risk, automatically prompting adjustment of an environmental aspect associated with the user, the environmental aspect comprising at least one of: lighting, temperature, or an audio stimulus.

7. The method of claim 1, further comprising determining a degree of cardiovascular parameter value dip associated with the second time period, wherein the cardiovascular metric is determined based on the degree of cardiovascular parameter value dip.

8. The method of claim 1, wherein the cardiovascular parameter value comprises at least one of a blood pressure value or a heart rate value.

9. The method of claim 1, further comprising, for each of the first and second time periods, fitting a harmonic cosinor model to the PPG dataset associated with the respective time period, wherein the cardiovascular parameter value of the user associated with the respective time period is determined based on the fitted harmonic cosinor model.

10. The method of claim 9, wherein the harmonic cosinor model is selected based on the respective time period.

11. The method of claim 1, further comprising automatically providing a medical recommendation based on the cardiovascular metric.

12. The method of claim 1, further comprising automatically facilitating a digital communication between the user and a care provider based on the cardiovascular metric.

13. The method of claim 1, further comprising determining an optimal number of time periods based on the chronobiological model, wherein a cardiovascular parameter value of the user is determined for each of the time periods.

\* \* \* \* \*